United States Patent
Bauer et al.

(10) Patent No.: US 7,323,481 B2
(45) Date of Patent: Jan. 29, 2008

(54) THIAZOLIDINEDIONES ALONE OR IN COMBINATION WITH OTHER THERAPEUTIC AGENTS FOR INHIBITING OR REDUCING TUMOUR GROWTH

(75) Inventors: Sabine Bauer, Munich (DE); Markus Meyer, Neuenburg (DE); Tobias Schnitzer, Munich (DE); Christine Schuell, Penzberg (DE); Hans-Peter Wolff, Weinheim (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/474,443

(22) PCT Filed: Apr. 4, 2002

(86) PCT No.: PCT/EP02/03746

§ 371 (c)(1),
(2), (4) Date: May 12, 2004

(87) PCT Pub. No.: WO02/080913

PCT Pub. Date: Oct. 17, 2002

(65) Prior Publication Data

US 2005/0176787 A1 Aug. 11, 2005

(30) Foreign Application Priority Data

Apr. 6, 2001 (EP) .................................. 01107820

(51) Int. Cl.
*A61K 31/425* (2006.01)
(52) U.S. Cl. ..................................................... 514/369
(58) Field of Classification Search ............... 514/365, 514/369
See application file for complete search history.

(56) References Cited

U.S. PATENT DOCUMENTS 5,599,826 A * 2/1997 Mertens et al. ............. 514/364
6,258,832 B1 7/2001 Kuhnle et al.

6,441,185 B2 8/2002 Kuhnle et al.

FOREIGN PATENT DOCUMENTS

| WO | WO 94/27995 | 12/1994 |
|---|---|---|
| WO | WO 98/25598 | 6/1998 |
| WO | WO 98/42704 | 10/1998 |
| WO | WO 99/48529 | 9/1999 |
| WO | WO 00/18234 A1 | 4/2000 |
| WO | WO 00/30628 | 6/2000 |
| WO | WO 01/79202 | 10/2001 |
| WO | 02/13812 | * 2/2002 |

OTHER PUBLICATIONS

Beers, M.D. et al., The Merck Manual of Diagnosis and Therapy, 17th Edition (1999), Chapter 142/Overview of Cancer, pp. 973-980.*
Stedman's Medical Dictionary, 25th Edition, Williams & Wilkins, Baltimore, (1990), p. 955.*
Goodman &Gilman's, The Pharmacological Basis of Therapeutics, Ninth Edition, (1996), Calabresi et al., Section X, Chemotherapy of Neoplastic Diseases, pp. 1225-1232.*
Fürnsinn et al., Br. J. Pharmacol, 128 pp. 1141-1148 (1999).
Elstner, E., et al., Proc. Nat. Acad. Sci. USA 95 (1998) 8806-8811.
Iijima, K., et al., Biochem. Biophys. Res. Commun. 247 (1998) 353-356.
Kersten, S., et al., Nature 405 (2000) 421-424.
Kliewer, S.A., et al., Nature 358 (1992) 771-774.
Kubota, T., et al., Cancer Res. 58 (1998) 3344-3352.
Mueller, E., et al., Molecular Cell (1998) 465-470.
Pershadsingh, H.A., Exp. Opin. Invest. Drugs 8 (1999) 1859-1872.
Rami, H.K., and Smith, S.A., Exp. Opin. Ther. Patents 10 (2000) 623-634.
Sarraf, P., et al., Nat. Med. 4 (1998) 1046-1052.
Tontonoz., P., et al., Mol. Cell. Biol. 15 (1995) 351.
Tontonoz, P., et al., Proc. Nat. Acad. Sci. USA 94 (1997) 237-241.
Willson, T.M., et al., J. Med. Chem. 43 (2000) 527-550.
Mueller, E., et al., Proc. Natl. Acad. Sci. 97(2000) 10990-10995.

* cited by examiner

*Primary Examiner*—Ardin H. Marschel
*Assistant Examiner*—James D. Anderson
(74) *Attorney, Agent, or Firm*—George W. Johnston; Patricia S. Rocha-Tramaloni; Gene J. Yao

(57) ABSTRACT

Use of thiazolidinedione derivatives for the preparation of medicaments for inhibiting or reducing tumour growth or metastases, alone or in combination with an RXR agonist or well-known antitumour agent.

6 Claims, No Drawings

THIAZOLIDINEDIONES ALONE OR IN COMBINATION WITH OTHER THERAPEUTIC AGENTS FOR INHIBITING OR REDUCING TUMOUR GROWTH

FIELD OF THE INVENTION

The present invention relates to ligands that bind to and affect the peroxisome proliferator-activated receptor (PPAR) gamma as well as their therapeutic use alone or in combination with other therapeutic agents for inhibiting or reducing the growth of tumours.

BACKGROUND OF THE INVENTION

The peroxisome proliferator-activated receptors (PPARs) belong to the steroid receptor superfamily and, as such, are ligand activated transcription factors and exist in different subtypes and isoforms (see, for example, Pershadsingh, H. A., Exp. Opin. Invest. Drugs 8 (1999) 1859-1872; Willson, T. M., et al., J. Med. Chem. 43 (2000) 527-550; Kersten, S., et al., Nature 405 (2000) 421-424; Rami, H. K., and Smith, S. A., Exp. Opin. Ther. Patents 10 (2000) 623-634 and references cited therein). Three subtypes of PPARs (PPAR alpha, PPAR gamma and PPAR delta) have been identified and cloned from mouse and human. PPAR gamma, existing in three isoforms (termed PPAR gamma 1, PPAR gamma 2 and PPAR gamma 3), is the most extensively studied and is considered to be of clinical importance. The antidiabetic activity of different natural and synthetic ligands is correlated with the activation of this receptor.

Thiazolidinediones are a class of compounds that selectively activate PPAR gamma and thus serve as oral insulin-sensitizing agents that lower the blood lipid and blood glucose levels. Exemplary thiazolidinediones are troglitazone, pioglitazone, ciglitazone, rosiglitazone, englitazone, BM 13.1258, BM 15.2054 and derivatives thereof. The PPAR gamma activity of BM 13.1258 and BM 15.2054 has already been reported by Fürnsinn, C., et al. (Br. J. Pharmacol. 128 (1999) 1141-1148) which is incorporated by reference.

Apart from the recognised importance of PPAR gamma agonists in the area of metabolic diseases the discovery of PPAR gamma-dependent modulation of the cell cycle has led to a substantial number of different approaches for the treatment of proliferative diseases utilising compounds that bind to and thereby activate PPAR gamma. In addition to adipose tissue, PPAR gamma is reported to be highly expressed in several cancer cell lines including liposarcoma (Iijima, K., et al., Biochem. Biophys. Res. Commun. 247 (1998) 353-356), breast cancer (Mueller, E., et al., Molecular Cell (1998) 465-470; Elstner, E., et al., Proc. Nat. Acad. Sci. USA 95 (1998) 8806-8811), prostate cancer (Kubota, T., et al., Cancer Res. 58 (1998) 3344-3352) and colon cancer (Sarraf, P., et al., Nat. Med. 4 (1998) 1046-1052).

Additionally, troglitazone as a specific PPAR gamma agonist from the thiazolidinedione class is known to inhibit the growth of human cancer cells in vitro and in vivo which is disclosed in some patent applications (WO 98/25598, WO 00/18234, WO 00/30628) and described in a number of papers. In addition, thiazolidinediones including troglitazone have been shown to induce terminal differentiation in human liposarcoma cells (Tontonoz, P., et al., Proc. Nat. Acad. Sci. USA 94 (1997) 237-241). The differentiation of malignant cells represents an ideal concept for treating cancer as opposed to a cell death mediated mechanism.

The PPARs belong to type II steroid receptors that are functionally distinct from the classical steroid receptors and do not bind to their respective binding site to form a homodimer. PPAR gamma heterodimerizes with at least one other member of the steroid receptor family, the retinoid acid receptors, namely RXR alpha (Kliewer, S. A., et al., Nature 358 (1992) 771-774; Tontonoz, P., et al., Mol. Cell. Biol. 15 (1995) 351).

The combination of specific PPAR gamma ligands and RXR alpha ligands activates both receptors, leads to an additive stimulation of differentiation and results in a synergistic inhibition of the cancer cell growth (Tontonoz, P., et al., Proc. Nat. Acad. Sci. USA 94 (1997) 237-241; Elstner, E., et al., Proc. Nat. Acad. Sci. USA 95 (1998) 8806-8811).

DETAILED DESCRIPTION OF THE INVENTION

The present invention is based on the unexpected finding that thiazolidinediones of formula I can be administered alone or in combination with other therapeutic agents to inhibit or reduce the growth of tumours in vivo. Activation of PPAR gamma in endothelial tissue using suitable natural or synthetic ligands is reported to inhibit the formation of new blood vessels and thereby inhibiting angiogenesis. By reducing the vascularization the tumor size and growth can be inhibited or reduced.

In one aspect, the present invention relates to compounds of the general formula I:

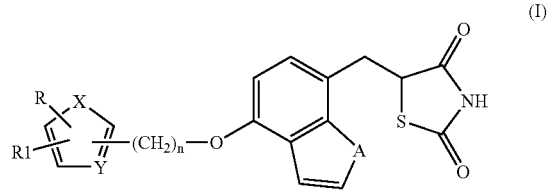

wherein

A is CH=CH or S;

R is selected from naphthalenyl, thienyl or phenyl which could be mono- or disubstituted with $C_1$-$C_3$ alkyl, $CF_3$, $C_1$-$C_3$ alkoxy, F, Cl, Br or OH;

R1 is selected from H or $C_1$-$C_6$ alkyl;

X is selected from S, O or $NR'_2$ where R' refers to H or $C_1$-$C_6$ alkyl;

Y is CH or N;

n is an integer from 1-3.

The enantiomers of compounds of the general formula I, their diastereomers, racemates and mixtures thereof are also included in the present invention as well as physiologically tolerated salts and solvates of these compounds with pharmaceutically acceptable, non-toxic inorganic and organic acids and bases.

Compounds of the general formula I have already been disclosed in other patent applications (WO 94/27995 and WO 98/42704) which are incorporated by reference.

Preferred compounds of formula I are those in which A is an ethylene group or sulfur, R is thienyl, unsubstituted or monosubstituted phenyl, R1 is methyl, W is oxygen, X is oxygen, Y is nitrogen and n is 2.

The most preferred compounds are:
(1) 5-{4-[2-(5-Methyl-2-phenyloxazol-4-yl)-ethoxy]-benzo[b]thiophen-7-ylmethyl}-thiazolidine-2,4-dione=BM 13.1258
(2) 5-{4-[2-(5-Methyl-2-(thien-2-yl)oxazol-4-yl)-ethoxy]-benzo[b]thiophen-7-ylmethyl}-thiazolidine-2,4-dione=BM 15.2054
(3) 5-{4-[2-(5-Methyl-2-phenyloxazol-4-yl)-ethoxy]-naphth-1-ylmethyl}-thiazolidine-2,4-dione
(4) 5-{4-[2-(2-(4-Fluorophenyl)-5-methyloxazol-4-yl)-ethoxy]-benzo[b]thiophen-7-ylmethyl}-thiazolidine-2,4-dione
(5) 5-{4-[2-(2-(4-Chlorophenyl)-5-methyloxazol-4-yl)-ethoxy]-benzo[b]thiophen-7-ylmethyl}-thiazolidine-2,4-dione
(6) 5-{4-[2-(5-Methyl-2-(4-trifluoromethylphenyl)-oxazol-4-yl)-ethoxy]-benzo[b]thiophen-7-ylmethyl}-thiazolidine-2,4-dione
(7) 5-{4-[2-(2-(4-Hydroxyphenyl)-5-methyloxazol-4-yl)-ethoxy]-benzo[b]thiophen-7-ylmethyl}-thiazolidine-2,4-dione
(8) 5-{4-[2-(5-Methyl-2-(thien-2-yl)-oxazol-4-yl)-ethoxy]-naphthalen-1-ylmethyl}-thiazolidine-2,4-dione.

Examples (7) and (8) which are novel and not disclosed in WO 94/27995 or WO 98/42704 have been prepared according to standard synthesis strategies described within these patent applications.

Example 7: m.p.=127-132° C. (decomp.)
Example 8: m.p.=158-159° C.

In another aspect, the present invention relates to the administration of a thiazolidinedione of formula I and an RXR ligand in a synergistic manner.

A wide variety of natural and synthetic RXR ligands as for example all-trans-retinoic acid, 9-cis-retinoic acid, phytanic acid, fenretinide, tazarotene and other derivatives of retinoic acid are known compounds that are described and disclosed in various papers and patents and thus appropriate to be used as RXR agonists in the method of the present invention.

In order to produce pharmaceutical acceptable dosage forms, the compound of formula I and optionally an RXR agonist are mixed in a known manner with suitable pharmaceutical carrier substances, aromatics, flavouring and dyes and are formed for example into tablets or coated tablets or they are suspended or dissolved in water or an oil such as e.g. olive oil in addition to appropriate auxliary substances.

The compound of formula I and optionally the RXR agonist can be administered orally or parenterally in a liquid or solid form. Water is preferably used as the medium that contains the stabilizing agents, solubilizers and/or buffers which are usually used for injection solutions. Such additives are for example tartrate or borate buffers, ethanol, dimethylsulfoxide, complexing agents (such as ethylenediaminetetraacetic acid), high molecular polymers (such as liquid polyethylene oxide) for regulation of the viscosity or polyethylene derivatives of sorbitol anhydrides.

Solid carrier substances are e.g. starch, lactose, mannitol, methylcellulose, talcum, highly dispersed silicic acid, higher molecular fatty acids (such as stearic acid), gelatine, agar-agar, calcium phosphate, magnesium stearate, animal and vegetable fats or solid high polymers (such as polyethylene glycols). Suitable formulations for the oral route can if desired contain flavourings and sweeteners.

The compound of formula I and optionally the RXR agonist are suitable to be administered also intravenously or by intramuscular, intraperitoneal, subcutaneous, intra-articular, intrasynovial, intrathecal, topical, intratumoral, peritumoral, intralesional, perilesional or inhalation routes.

The administered dose for the prevention or treatment of a disease depends on the age, the health and the weight of the patient, the extent of the disease, the type of treatments which are possibly being carried out concurrently, the frequency of treatment and the type of the desired effect. The daily dose of the active compound is usually 0.1 to 200 mg/kg body weight. Normally 0.5 to 100 mg/kg/day and preferably 1 to 50 mg/kg/day in one or several applications per day are effective in order to obtain the desired results. The compound of formula I and the RXR agonist are administered as a mixture of therapeutic agents with a typical ratio of 100:1 to 1:100 and a preferable ratio of 10:1 to 1:10.

The compounds of formula I and optionally the RXR agonist are useful in treatment of various diseases and disorders that have been discovered to be a result of neoplastic cell proliferation. Such states include, for example, breast cancer, colon cancer, prostate cancer and liposarcoma.

In yet another aspect, the method of the present invention involves the use of compounds of the general formula I in combination with one or more other anti-tumor agents such as: cisplatin, carboplatin, cyclophosphamide, docetaxel, paclitaxel, bleomycin, 5-fluorouracil, 5'-deoxy-5-fluoro-N-pentyloxycarbonyl-cytidine, doxorubicine or tamoxifen.

The main purpose for using a compound of formula I and a conventional antineoplastic compound is to lower the doses of the potentially toxic chemotherapeutic agent while still causing tumor regression. Thiazolidinediones in general and compounds of formula I are known to be non-toxic substances. Thus, the application of a compound of formula I in addition to a conventional antineoplastic compound is expected to require up to a 100 fold decreased dosage of the toxic chemotherapeutic agent for similar efficacy compared to the chemotherapeutic agent alone.

Pharmacological Test Results

It has been found that compounds of formula I, exemplary for BM 13.1258 and BM 15.2054, inhibit cell proliferation in human cancer cells of various tissue origins, e.g. in breast cancer, colon cancer and prostate cancer. Furthermore, it was demonstrated that the compounds of formula I are able to halt tumour growth in human xenograft models. Surprisingly, it was found that BM 13.1258 and BM 15.2054 reduce the metastatic load in these models, whereas troglitazone did not show this effect.

Female SCID beige mice were inoculated subcutaneously with $1\times10^6$ CX-1 human colon carcinoma cells. For 42 days 10 animals per group were orally treated with troglitazone, BM 13.1258 or BM 15.2054 (suspension in 0.5% methylcellulose). The development of tumor volume (measured in $mm^3$) was determined on day 45. Furthermore, following autopsy the lungs were histologically inspected for micrometastases. Inhibition of tumor growth and inhibition of number of pulmonal metastases were calculated as 100 minus tumor volume or number of metastases of the test group divided by that of the vehicle group expressed as a percentage. PPAR gamma stimulating activity of the compounds alone and in combination with the RXR specific agonist 9-cis retinoic acid were determined in accordance with a known method (Furnsinn, C., et al., Br. J. Pharmacol. 128 (1999) 1141-1148). The relative activation of PPAR-mediated gene expression is given as x-fold stimulation compared to DMSO-treated cells (activation=1).

As demonstrated by Table 1 administration of the thiazolidinediones BM 13.1258 is effective in reducing the size of colon carcinoma in SCID beige mice. This anti-tumor effect is superior to that of troglitazone.

TABLE 1

Average tumor volume and inhibition compared to vehicle treated controls

| Treatment groups | Dose [mg/kg] | Mean tumor volume [mm³] | Inhibition relative to vehicle group |
|---|---|---|---|
| Vehicle | — | 1003 | — |
| BM 15.2054 | 10 | 702 | 30% |
| BM 15.2054 | 50 | 719 | 28% |
| BM 13.1258 | 50 | 604 | 40% |
| Troglitazone | 200 | 804 | 20% |

Table 2 shows that by BM 15.2054 the number of lung metastases is significantly ($p<0.05$) reduced compared to the vehicle group. Troglitazone treatment on the contrary did not diminish the number of lung metastases.

TABLE 2

Number of metastases per group and inhibition compared to vehicle treated controls

| Treatment groups | Dose [mg/kg] | Number of metastases | Inhibition relative to vehicle group |
|---|---|---|---|
| Vehicle | — | 326 | — |
| BM 15.2054 | 10 | 216 | 34% |
| BM 15.2054 | 50 | 223 | 32% |
| Troglitazone | 200 | 352 | −8% |

Table 3 demonstrates that the combination of compounds of formula I with the RXR agonist 9-cis retinoic acid results in a 4-to 7-fold higher stimulation of PPAR gamma-mediated gene expression than BM 13.1258 or BM 15.2054 alone. This observed effect is not only additive, but highly synergistic.

TABLE 3

Synergistic activation of PPAR gamma in combination with 9-cis retinoic acid (RA)

| | no | BM 13.1258 | | BM 15.2054 | |
|---|---|---|---|---|---|
| thiazolidinedione | | $10^{-7}$ M | $10^{-6}$ M | $10^{-7}$ M | $10^{-6}$ M |
| no 9-cis RA | 1 | 3.7 | 4.0 | 4.3 | 3.5 |
| 9-cis RA ($10^{-6}$ M) | 4.1 | 24.4 | 28.0 | 15.6 | 18.5 |

LIST OF REFERENCES

Elstner, E., et al., Proc. Nat. Acad. Sci. USA 95 (1998) 8806-8811
Fürnsinn, C., et al., Br. J. Pharmacol. 128 (1999) 1141-1148
Iijima, K., et al., Biochem. Biophys. Res. Commun. 247 (1998) 353-356
Kersten, S., et al., Nature 405 (2000) 421-424
Kliewer, S. A., et al., Nature 358 (1992) 771-774
Kubota, T., et al., Cancer Res. 58 (1998) 3344-3352
Mueller, E., et al., Molecular Cell (1998) 465-470
Pershadsingh, H. A., Exp. Opin. Invest. Drugs 8 (1999) 1859-1872
Rami, H. K., and Smith, S. A., Exp. Opin. Ther. Patents 10 (2000) 623-634
Sarraf, P., et al., Nat. Med. 4 (1998) 1046-1052
Tontonoz, P., et al., Mol. Cell. Biol. 15 (1995) 351
Tontonoz, P., et al., Proc. Nat. Acad. Sci. USA 94 (1997) 237-241
Willson, T. M., et al., J. Med. Chem. 43 (2000) 527-550
WO 00/18234
WO 00/30628
WO 94/27995
WO 98/25598
WO 98/42704

The invention claimed is:

1. A method of inhibiting or reducing colon carcinoma tumor growth or metastases comprising administering, to a patient in need thereof, a therapeutically effective amount of a compound selected from the group consisting of:
    (5-{4-[2-(5-Methyl-2-phenyloxazol-4-yl)-ethoxy]-benzo[b]thiophen-7-ylmethyl}-thiazolidine-2,4-dione);
    (5-{4-[2-(5-Methyl-2-(thien-2-yl)oxazol-4-yl)-ethoxy]-benzo[b]thiophen-7-ylmethyl}-thiazolidine-2,4-dione);
    the enantiomers, diastereomers, racemates and mixtures of such compounds; and
    the salts of such compounds with pharmaceutically acceptable acids and bases.

2. The method according to claim 1, wherein the compound is selected from the group consisting of
    5-{4-[2-(5-Methyl-2-phenyloxazol-4-yl)-ethoxy]-benzo[b]thiophen-7-ylmethyl}-thiazolidine-2,4-dione; and
    5-{4-[2-(5-Methyl-2-(thien-2-yl)oxazol-4-yl)-ethoxy]-benzo[b]thiophen-7-ylmethyl}-thiazolidine-2,4-dione.

3. The method according to claim 1, further comprising administering, to a patient in need thereof, a therapeutically effective amount of an RXR agonist.

4. The method according to claim 3, wherein the RXR agonist is 9-cis-retinoic acid.

5. The method according to claim 1, further comprising administering, to a patient in need thereof, a therapeutically effective amount of an anti-tumor agent.

6. The method according to claim 5, wherein the antitumor agent is selected from the group consisting of cisplatin, carboplatin, cyclophosphamide, docetaxel, paclitaxel, bleomycin, 5-fluorouracil, 5'-deoxy-5-fluoro-N-pentyloxycarbonyl-cytidine, doxorubicine and tamoxifen.

* * * * *